(12) United States Patent
Zhang et al.

(10) Patent No.: US 10,328,200 B2
(45) Date of Patent: Jun. 25, 2019

(54) MULTIFUNCTION CAPACITIVE SENSOR FOR MEDICAL PUMP

(71) Applicant: Zyno Medical, LLC, Natick, MA (US)

(72) Inventors: Mei Zhang, Sharon, MA (US); Chaoyoung Lee, Weston, MA (US)

(73) Assignee: Zyno Medical, LLC, Natick, MA (US)

( * ) Notice: Subject to any disclaimer, the term of this patent is extended or adjusted under 35 U.S.C. 154(b) by 358 days.

(21) Appl. No.: 15/002,709

(22) Filed: Jan. 21, 2016

(65) Prior Publication Data

US 2016/0136354 A1     May 19, 2016

Related U.S. Application Data

(62) Division of application No. 14/104,371, filed on Dec. 12, 2013, now Pat. No. 9,327,072.

(60) Provisional application No. 61/736,778, filed on Dec. 13, 2012.

(51) Int. Cl.
    *A61M 5/00*     (2006.01)
    *A61M 5/168*     (2006.01)
    *A61M 5/50*     (2006.01)
    *A61M 5/142*     (2006.01)
    *A61M 5/36*     (2006.01)

(52) U.S. Cl.
    CPC .... *A61M 5/16831* (2013.01); *A61M 5/14228* (2013.01); *A61M 5/365* (2013.01); *A61M 5/5086* (2013.01); *A61M 2205/3317* (2013.01)

(58) Field of Classification Search
    CPC . G06F 19/3468; A61M 5/365; A61M 5/5086; A61M 5/16831; A61M 2005/16863; A61M 2005/16868; A61M 2005/16872; A61M 2039/1005; A61M 2205/0227; A61M 2205/14
See application file for complete search history.

(56) References Cited

U.S. PATENT DOCUMENTS

| | | | | |
|---|---|---|---|---|
| 3,911,902 | A * | 10/1975 | Delpy | A61B 5/0215 600/488 |
| 4,650,457 | A * | 3/1987 | Morioka | A61M 1/1086 128/DIG. 3 |
| 4,981,467 | A * | 1/1991 | Bobo, Jr. | A61M 5/365 604/122 |
| 5,152,424 | A * | 10/1992 | Weinreb | A61F 9/0008 222/1 |
| 5,464,391 | A * | 11/1995 | DeVale | A61M 3/0258 128/DIG. 12 |
| 6,017,318 | A * | 1/2000 | Gauthier | A61M 5/1723 600/578 |
| 6,731,216 | B2 * | 5/2004 | Ho | A61M 5/14228 340/591 |
| 7,194,297 | B2 * | 3/2007 | Talpade | A61B 5/055 324/300 |
| 9,327,072 | B2 * | 5/2016 | Zhang | A61M 5/14228 |

(Continued)

*Primary Examiner* — William R Carpenter
(74) *Attorney, Agent, or Firm* — Boyle Fredrickson S.C.

(57) ABSTRACT

A medical pump or the like provides for a multi-function flow monitor that provides for capacitive plates positioned on opposite sides of the IV line to sense changes in the electrical environment within the IV line to deduce IV line pressure, the presence of IV fluid bubbles, the presence of the IV line within the pump, and/or correct pump operation. Each of these conditions may be determined by different analysis of the capacitance across the capacitive plates.

14 Claims, 3 Drawing Sheets

(56) References Cited

U.S. PATENT DOCUMENTS

| | | | |
|---|---|---|---|
| 2005/0145008 A1* | 7/2005 | Vanderveen | A61M 5/14228 73/1.57 |
| 2006/0173419 A1* | 8/2006 | Malcolm | A61M 5/16827 604/246 |
| 2007/0083153 A1* | 4/2007 | Haar | A61M 5/14244 604/67 |
| 2007/0179435 A1* | 8/2007 | Braig | A61B 5/145 604/66 |
| 2012/0283630 A1* | 11/2012 | Lee | A61M 5/16827 604/65 |

* cited by examiner

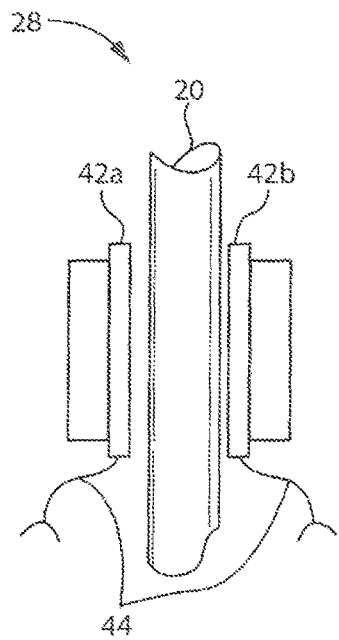
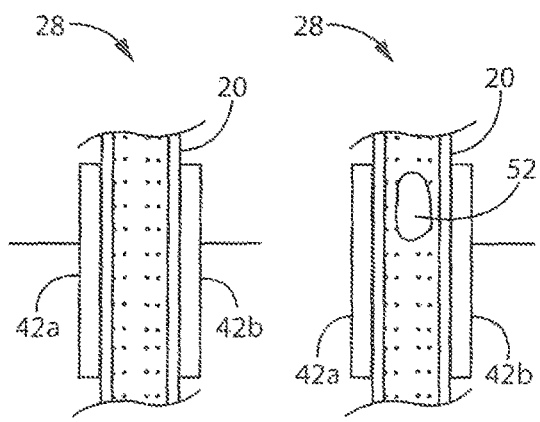
FIG. 3
FIG. 4A   FIG. 4B
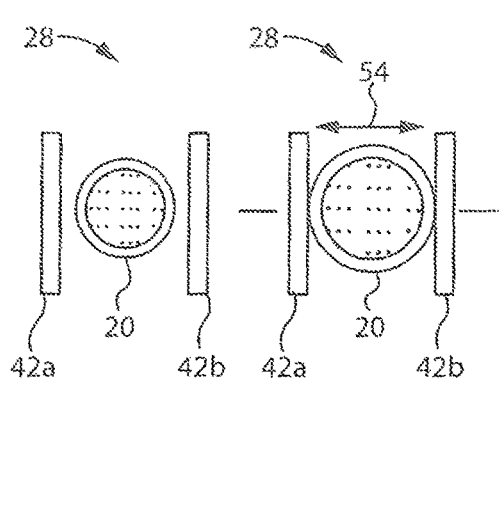
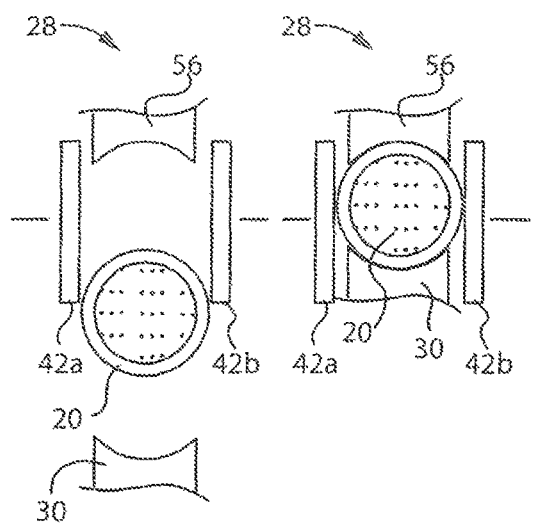
FIG. 5A   FIG. 5B   FIG. 6A   FIG. 6B

US 10,328,200 B2

MULTIFUNCTION CAPACITIVE SENSOR FOR MEDICAL PUMP

CROSS-REFERENCE TO RELATED APPLICATIONS

This application is a divisional application of U.S. patent application Ser. No. 14/104,371 filed Dec. 12, 2013 and hereby incorporated by reference, which claims the benefit of U.S. provisional application 61/736,778 filed Dec. 13, 2012 and hereby incorporated by reference.

BACKGROUND OF THE INVENTION

The present invention relates to medical pumps for the delivery of medicines to patients under controlled rates and dosages and in particular to a pump sensor for characterizing this flow.

Medical pumps, such as syringe pumps or peristaltic infusion pumps, are known for computer-controlled delivery of medication or contrast agents (henceforth drugs) to patients over a period of time. Typically the drug is delivered in a syringe (for a syringe pump) or a flexible bag (for peristaltic infusion pump) that may be connected to an IV line attached to a needle for insertion into the patient. When a nurse or other health care professional ministering to the patient receives the drug, the healthcare professional reviews the drug description for correctness and enters the desired dose and rate into the pump. The syringe or IV line must then be mechanically connected to the pump mechanism and the mechanism activated to begin pumping. Failure to properly install, set up or connect the drug container properly to the pump can raise safety issues.

During the pumping operation, the drug flow may be automatically monitored by one or more sensors that detect proper operation of the medical pump. Different such sensors may detect, for example, flow rate, line pressure, the presence of bubbles in the drug and the like.

SUMMARY OF THE INVENTION

The present invention provides a sensor for medical pumps that may simultaneously detect combinations or sub combinations of: flow rate, IV line pressure, IV line bubbles, and/or proper seating of the IV line within the pump. In a principal embodiment, opposed capacitor plates are installed on opposite walls of the IV line. The distance between the two plates is greater than the outer diameter of the IV line. Pressure changes in the IV line are manifest in low amplitude capacitance changes as more fluid fills the space between the two plates with increased pressurization of the IV line. Bubbles are detected by the same sensor by more abrupt capacitance changes caused by fundamental changes in the permittivity of the dielectric between the plates (air vs. fluid). Proper seating of the IV line may be provided by detecting a fluid filled IV line between the plates such as abruptly affects the intervening permittivity before pumping.

It should be understood that the invention is not limited in its application to the details of construction and arrangements of the components set forth herein. The invention is capable of other embodiments and of being practiced or carried out in various ways. Variations and modifications of the foregoing are within the scope of the present invention. It also being understood that the invention disclosed and defined herein extends to all alternative combinations of two or more of the individual features mentioned or evident from the text and/or drawings. All of these different combinations constitute various alternative aspects of the present invention. The embodiments described herein explain the best modes known for practicing the invention and will enable others skilled in the art to utilize the invention.

BRIEF DESCRIPTION OF THE FIGURES

FIG. 3 is a fragmentary front elevational view of the sensor of the present invention showing two capacitor plates flanking an IV line inserted therebetween;

FIGS. 4a and 4b are simplified front elevational views similar to that of FIG. 3 showing passage of an air bubble between the capacitor plates;

FIGS. 5a and 5b are simplified top cross-sectional views of the IV line and capacitor plates of FIG. 3 showing increased, percentage of the cross section being filled with fluid with increased pressure of the IV line;

FIGS. 6a and 6b are simplified top cross-sectional views similar to FIGS. 5a and 5b showing displacement of the IV line between the capacitor plates prior to proper seating by closure of the door of FIG. 1;

DETAILED DESCRIPTION OF THE PREFERRED EMBODIMENT

Figure 1:
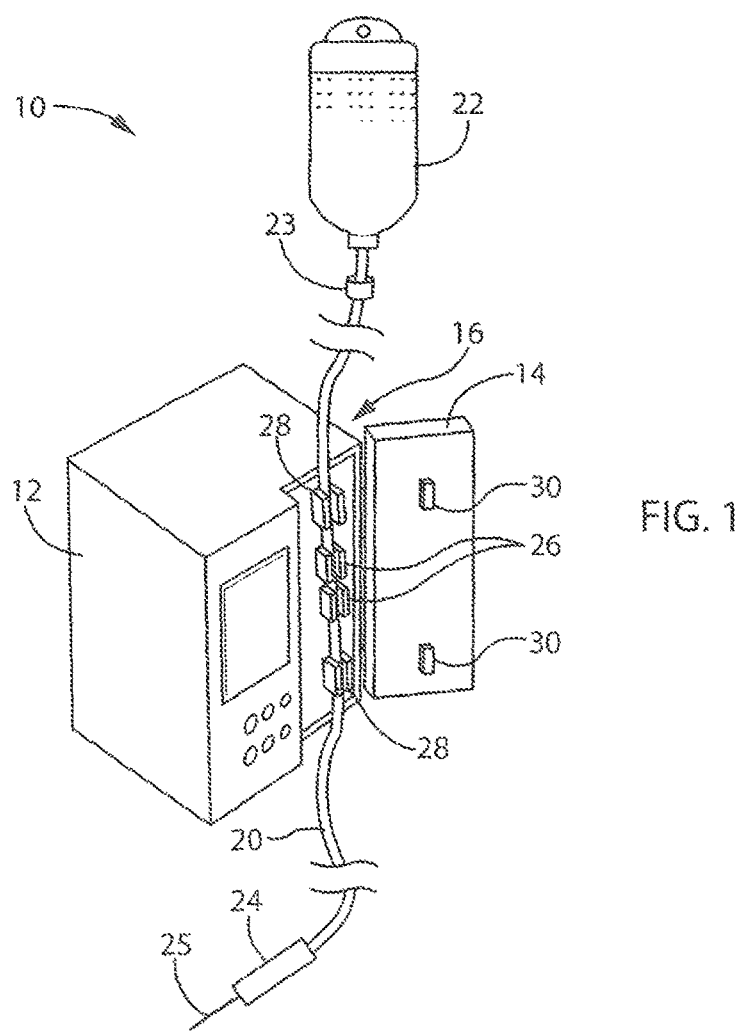
FIG. 1 is a simplified perspective representation of a medical pump employing the sensor of the present invention for an IV line that may be contained within a portion of the pump coverable by a pump door.

Referring now to FIG. 1, a medical pump 10, for example an infusion pump, may provide for a housing 12 having a front opening door 14 that may reveal a pump compartment 16. An IV line 20 may be threaded through the pump compartment 16 for pumping and monitoring of an IV fluid from a sterile connector 23 to an IV bag 22 through the IV line 20 to be delivered to through a sterile connector 24 to a hypodermic needle 25 or similar connection to a patient (not shown). The IV line 20 may be a highly compliant material that may be sterilizable and is, preferably, non-Pyrogenic, non-DEHP and latex-free. One such material is silicone rubber which provides for high compliance as will be desired for pressure sensing to be described below. Another example is non-DEHP PVC material.

The pump compartment 16 may hold peristaltic pump elements 26 through which the IV line 20 may be threaded for controllably pumping liquid therethrough according to techniques understood in the art. Generally such pumps operate with positive displacement to provide a precise flow amount with each pump cycling. A sensor element 28 per the present invention may be placed above and/or below the pump elements 26 to also receive the IV line therein. An inside of the door 14 covering the pump compartment 16 may provide for seating features 30 that will ensure proper seating of the IV line 20 within the peristaltic pump elements 26 and sensors 28 when the door 14 is closed, as will be described further below.

Figure 2:
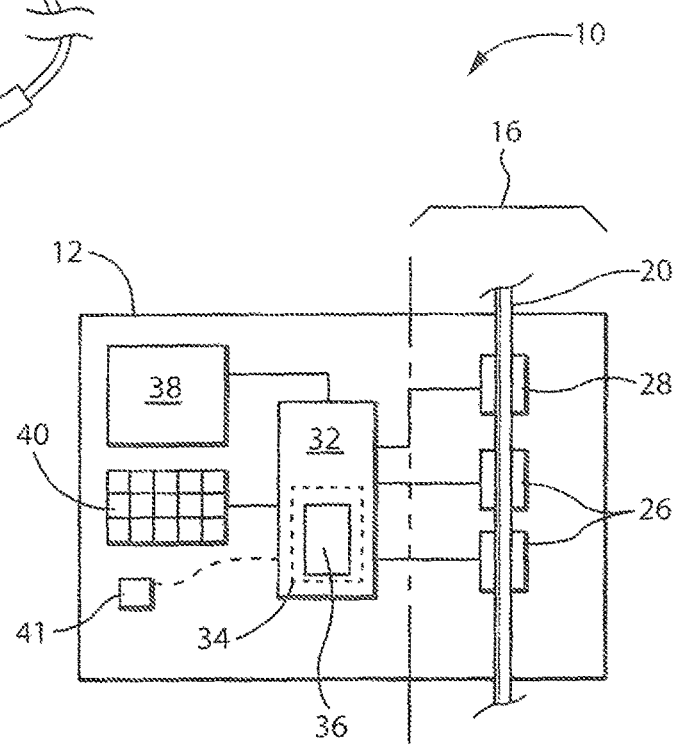
FIG. 2 is a block diagram of the principal elements of the pump including a processor for monitoring the sensor of the present invention using a stored program.

Referring now to FIG. 2, the pump 10 may include a controller 32 (which may be a microprocessor based circuit) having a memory 34 for holding a stored operating program 36 controlling operation of the pump 10 according to a desired dose and rate of desired drug delivery through the IV line 20. In particular, the controller 32 may use the data in the memory 34 to control the pump elements 26 in the pump compartment 16, for example, by successively compressing the pump elements 26 about the IV line 20 for peristaltically moving fluid through the IV line 20.

The controller 32 may further communicate with the sensor element 28 of the present invention for receiving a signal therefrom. Generally, the controller 32 executing the stored program 36 may interpret the signal from the sensor element 28 to monitor pressure in the IV line 20 installed in the pump compartment 16 for detection of blockage or other pumping irregularities. In addition, the signal from the sensor element 28 may be monitored to detect bubbles in the IV line 18 and to detect proper seating of the IV line 20 in the sensor element 28, as will be described below.

The controller 32 may also communicate with a display screen 38 for displaying various programming and operating parameters of the medical pump 10 and a switch array 40 for inputting data, for example, for programming or initiating or stopping of the pumping action into the medical pump 10 for use by the controller 32.

The controller 32 may also communicate with an alarm 41, for example an audio, display, or wireless transmitter system for communicating an alarm to a user.

Referring now to FIG. 3, the sensor element 28 may provide a first set of opposed conductive plates 42a and 42b in parallel opposition across a diameter of a vertically extending IV line 20 inserted therebetween in the pump compartment 16. Each of the conductive plates 42a and 42b may be connected by leads 44 to circuitry that may measure the capacitance between these plates 42a and 42b using conventional techniques, for example a frequency counting oscillator employing the capacitance between the plates 42a and 42b to control an electrically resonant circuit oscillator frequency, or an integrator using the capacitance between the plates 42a and 42b to affect an integrator time constant and measuring the value of the integration at a fixed time period after a reset signal.

The conductive plates 42a and 42b are preferably mounted to the housing 12 in fixed opposition across the diameter of the IV line 20 with a separation slightly larger than the diameter of an unpressurized IV line 20. It will be understood generally that the capacitance between the plates 42a and 42b will be a function of their area and their separation, which remains substantially fixed and the effective dielectric constant (permittivity) between the plates which will be determined by the material of the IV line 20 and predominantly by the liquid contained therein and the diameter of the IV line 20.

Referring now to FIG. 4a, during normal operation of the pump 10, the space within the tube 20 between the plates 42a and 42b will be occupied primarily with a drug whose principal component is water having a known and substantially constant permittivity. As a result, during normal operation, there will be a substantially constant dielectric between the plates 42a and 42b. Referring to FIG. 4b, however, a bubble 52 passing through the tube 20 between the plates 42a and 42b will substantially change the dielectric between the plates 42a and 42b based on the significant differences between the dielectric constant of water and air. This bubble 52 will cause an abrupt decrease in the capacitance between the plates 42a and 42b. Generally the permittivity of air is approximately 1 whereas the permittivity of water is approximately 80.4.

Referring now to FIG. 5a, when the drug within the IV line 20 between the plates 42a and 42b is at a low pressure, the walls of the IV line 20 may be contracted to a relatively smaller diameter under the natural elasticity of the material of the IV line 20. In contrast, as shown in FIG. 5b, an increase in pressure will expand the cross-section of the tubing 20 to a larger diameter decreasing the airspace between the plates 42a and 42h and supplanting it with a higher permittivity of water. Generally, this change in capacitance will be both slower and more subtle than the changing capacitance provided by the bubble 52 of FIG. 4b as discussed above. This effect provides a measure of pressure in the IV line 20.

Referring now to FIG. 6a, a rearward wall of the IV line 20 between the plates 42a and 42b may be spaced from a wall support 56 when the tube 20 is not fully inserted into the pump compartment 16 and therefore not fully inserted between the plates 42a and 42b. Proper location of the tube 20 between the plates 42a and 42b, as shown in FIG. 6b, will move the tube 20 back against the wall support 56 to be centered between the plates 42a and 42b. This centering will increase the capacitance between the plates 42a and 42b by increasing the high permittivity dielectric material centered between the plates 42a and 42b in contrast to the incomplete insertion of FIG. 6a thereby allowing a determination of proper seating of the tube 20 between the plates 42a and 42b from the capacitance therebetween. Generally this change in capacitance between the states of FIGS. 6a and 6b may be readily distinguished from a bubble 52 per the example of FIGS. 4a and 4b by its significant increase in capacitance for an extended duration as opposed to decreasing capacitance significantly for a short period. In addition, the changing capacitance caused by the change in states shown in FIGS. 6a and 6b will occur by design before actual pumping of liquid (proper closure of the door being a predicate for pump operation) further differentiating it from pressure changes or included bubbles.

Figures 7, 8:
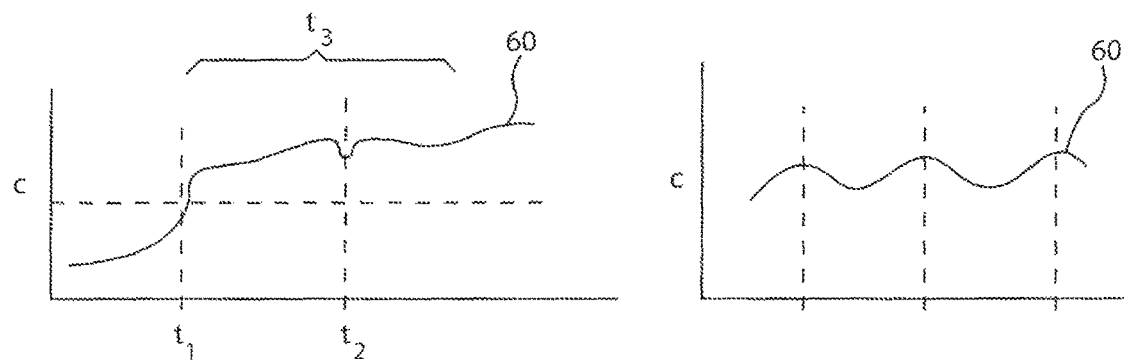
FIG. 7 is a plot of capacitance change across the capacitor plates of FIGS. 4-6 showing interpretation of those changes by the program of the processor of FIG. 2 for identifying proper seating of the IV line, pressure in the IV line, and bubbles in the IV line.
FIG. 8 is a plot similar to FIG. 7 showing fluctuations caused by operation of the positive displacement pump that may be counted to deduce flow rate.

Referring now to FIG. 7, an example capacitance signal 60 as a function of time monitored by the controller 32 of FIG. 2 may therefore detect three conditions, detecting at a time t1 a closure of the door caused by an increase in capacitance more than the predetermined threshold before operation of the pump. At time t2, a bubble may be detected as distinguished by a rapid decrease and then rapid increase in capacitance over a short period of time (e.g., less than ten seconds). Changes in pressure within the IV line may be determined over time range t3 (e.g., tens of seconds) after time t1 by slowly changing values in the capacitance (with increased capacitance values indicating increased pressures).

Referring now to FIG. 8, the capacitance signal 60 may be further analyzed to deduce the periodic pressure fluctuations caused by operation of pump elements 26 possibly augmented by frequency domain filtering at the pump cycle rate or synchronous filtering in phase with pump operation. Detecting these periodic pressure fluctuations of a predetermined amplitude can confirm operation of the pump elements 26 and counting the fluctuations can provide a measure of flow rate based on known volume displacement in each pump cycle of the pump elements 26. It will be appreciated that pressure sensing techniques other than capacitive sensing may also be used to deduce this flow rate including for example techniques that measure IV line deformation by optical or mechanical means.

A pressure range may be developed to indicate a desired pumping pressure and to sound the alarm in the event that the pressure exceeds or falls below this range. Likewise the presence of a bubble 52 may sound the alarm and stop the pump operation. Pump operation may be prevented from starting if the door has not been closed (indicated by not properly loaded tubing) as indicated by the detection at t1.

Figure 9:
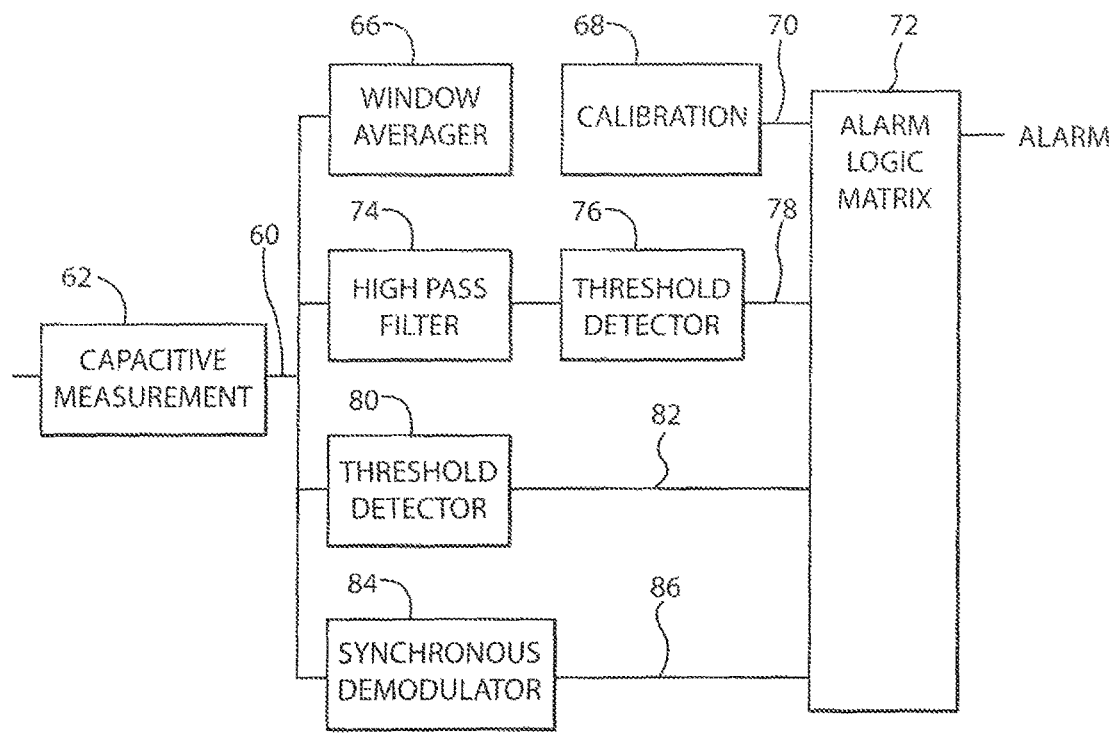
FIG. 9 is a process flow diagram of a program and circuitry executed by the medical pump of FIG. 1 for the processing of the capacitive signal into various sensed conditions of pressure, bubble presence, IV line presence, and pump operation.

Referring now to FIG. 9, the controller 32 may implement a capacitive sensing block 62 operating as described above to measure the capacitance between the capacitive sensor plates 42 as discussed. A measured capacitance signal 60 may then be processed in a number of different signal chains to reveal the desired information about IV fluid flow. The capacitance signal 60 may, for example, be received by a window averager 66 operating to take an average value of a predetermined time window of the measured capacitance signal 60, for example 10 seconds, to provide a smoothing of the capacitance value that may indicate the average pressure of the IV liquid free from influence by short-term perturbations. Alternative methods of providing the smoothing may include, for example, a low pass filter.

The output from the averager 66 may be provided to a calibration table 68 or the like converting capacitance values to internal pressure of the IV line 20 as may be empirically determined for particular types of IV tubing. The output of the calibration table 68 may then provide a pressure value 70 which may be received by an alarm logic matrix 72, for example, monitoring the pressure value 70 to detect overpressure indicating, for example, blockage of the IV line 20, or underpressure, for example, indicating an exhaustion of the liquid medicine from the IV bag 22. Either of these conditions may result in the presentation of an alarm to the user and may deactivate pumping by the pump.

The capacitance value 64 may alternatively or in addition be provided to a high pass filter 74 that accentuates the short-term perturbations in the capacitance signal 60 caused by a bubble. Adaptive filters or autocorrelation circuits or the like may be used alternatively as is understood in the art. The output of the high pass filter 74 is then provided to a threshold circuit 76 which determines whether any perturbation in the capacitance signal 60 is of the type such as would indicate a bubble has passed between the capacitive plates. It will be understood that the high pass filter removes the "DC" value of the capacitance signal 60 to permit this threshold circuit 76 to operate with a substantially constant threshold regardless of slowly changing overall pressure of the IV fluid. A bubble detection output 78 may also be provided to the alarm logic matrix 72 to provide an alarm or deactivate the pump.

The capacitance signal 60 may alternatively or in addition be sent to threshold circuit 80 detecting a threshold that will be exceeded when an IV line 20, even with low pressure, is in place in the pump housing between the plates 42. An IV line presence signal output 82 may also be provided to the alarm logic matrix 72 to provide either an alarm or to disable portions of the pump when an IV line 20 is not in place.

Capacitance signal 60 may finally be provided to a synchronous demodulator 84, for example, receiving a signal from the pump elements 26 to detect perturbations in the pressure shown in FIG. 8 caused by pump operation. Alternative demodulation systems may employ bandpass filtering and threshold detecting or the like. A pump confirmation signal 86 provided from the synchronous demodulator 84 is also received by the alarm logic matrix 72 to provide an alarm in the event of pump failure if the pump is not operating when otherwise indicated.

It will be appreciated that this sensor may be used to provide measures of all of these conditions as has been described above or any subset of these conditions. Further it will be appreciated that the sensor may be incorporated into the pump elements 26, for example, or that multiple such sensor elements 28 may be used.

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

References to "a microprocessor" and "a processor" or "the microprocessor" and "the processor," can be understood to include one or more microprocessors that can communicate in a stand-alone and/or a distributed environment(s), and can thus be configured to communicate via wired or wireless communications with other processors, where such one or more processor can be configured to operate on one or more processor-controlled devices that can be similar or different devices. Furthermore, references to memory, unless otherwise specified, can include one or more processor-readable and accessible memory elements and/or components that can be internal to the processor-controlled device, external to the processor-controlled device, and can be accessed via a wired or wireless network. Generally it will be appreciated that the microprocessor 32 may be accompanied with ancillary discrete circuitry as necessary and that the functions described above may be implemented wholly in discrete circuitry or in a combination of discrete circuitry and a microprocessor.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications, are hereby incorporated herein by reference in their entireties.

We claim:

1. A medical liquid delivery system comprising:
a housing adapted to receive an IV line within a housing portion wherein a received portion of the IV line is elastic to expand and contract in cross section with changes in pressure of liquid within the IV line;
first and second capacitive sensor electrodes positioned on the housing portion in fixed separation to flank the received IV line; and
control electronics configured to communicate with the first and second capacitive sensor electrodes to measure capacitance across the first and second capacitive sensor electrodes through the IV line and to measure a pressure of medical liquid within the received IV line based on changes in a dielectric material of the medical liquid between the first and second capacitive sensor electrodes with expansion of the IV line and to detect an overpressure in the IV line;
wherein the capacitive sensor electrodes are attached to the housing to be retained in the housing with removal of the IV line.

2. The medical liquid delivery system of claim 1 wherein the control electronics are configured to communicate with the capacitive sensor electrodes to measure capacitance across the capacitive sensor electrodes and to sense a presence of a liquid-filled received IV line between the capacitive sensor electrodes and further including an alarm wherein the control electronics are configured to trigger the alarm when the IV line is not present.

3. The medical liquid delivery system of claim 2 wherein the control electronics are configured to sense the presence of the liquid-filled received IV line by sensing an increase in water dielectric between the capacitive sensor electrodes with insertion of the IV line between the capacitive sensor electrodes.

4. The medical liquid delivery system of claim 1 wherein the control electronics includes calibration data relating change in capacitance to pressure-induced diametric distention of the received IV line for a particular IV line and is configured to determine the pressure of the medical liquid within the IV line by applying a sense-capacitive value to the calibration data and to provide an alarm when the determined pressure passes outside of a predetermined range.

5. The medical liquid delivery system of claim 4 wherein the control electronics includes signal filtering electronics configured to remove short-term perturbations in the measured capacitance across the capacitive sensor electrodes.

6. The medical liquid delivery system of claim 5 wherein the control electronics includes a threshold detector discriminating between capacitance of air versus a liquid filled IV line between the capacitive sensor electrodes.

7. The medical liquid delivery system of claim 1 further including an alarm and wherein the control electronics are configured to trigger the alarm based on the pressure of medical liquid within the received IV line.

8. The medical liquid delivery system of claim 1 further including a pump supported by the housing and adapted to receive a portion of the IV line and to pump liquid through the IV line and wherein the control electronics are further configured to communicate with the capacitive sensor electrodes to sense pressure fluctuation caused by operation of the pump.

9. The medical liquid delivery system of claim 1 wherein the IV line provides an attachment coupling for sterile attachment to an IV bag and for sterile attachment to a hypodermic needle.

10. A medical liquid delivery system comprising:
an elastic IV line compliant to expand and contract in cross section with changes in pressure of liquid within the IV line;
a housing adapted to receive the IV line within a housing portion;
at least two capacitive sensor electrodes positioned on the housing portion in fixed separation, the IV line positioned between the first and second capacitive sensor electrodes to flank the received IV line, and
control electronics configured to communicate with the first and second capacitive sensor electrodes to measure capacitance across the first and second capacitive sensor electrodes through the IV line to measure (1) a pressure of medical liquid within the IV line based on changes in a dielectric material of the medical liquid between the first and second capacitive sensor electrodes with expansion of the IV line and to detect an overpressure in the IV line and (2) a presence of a liquid-filled IV line between the first and second capacitive sensor electrodes.

11. The medical liquid delivery system of claim 10 wherein the pressure of medical liquid within the IV line is sensed by sensing a dielectric of the medical liquid between the capacitive sensor electrodes to measure diametric distention of the received IV line.

12. The medical liquid delivery system of claim 10 wherein the presence of a liquid-filled IV line between the capacitive sensor electrodes is sensed by sensing a threshold change in permittivity between air and water.

13. The medical liquid delivery system of claim 10 further including an alarm wherein the control electronics are further configured to communicate with the capacitive sensor electrodes and to trigger the alarm when the IV line is not present.

14. The medical liquid delivery system of claim 10 further including a pump supported by the housing and receiving a portion of the IV line to pump liquid through the IV line and wherein the control electronics are further configured to communicate with the capacitive sensor electrodes and to disable the pump when the IV line is not present.

* * * * *